United States Patent [19]

Khanna et al.

[11] Patent Number: 4,956,274

[45] Date of Patent: Sep. 11, 1990

[54] REAGENT STABILIZATION IN ENZYME-DONOR AND ACCEPTOR ASSAY

[75] Inventors: Pyare L. Khanna, Fremont; Robert Dworschack, Antioch; Phillip Ruprecht, Albany, all of Calif.

[73] Assignee: Microgenics Corporation, Concord, Calif.

[21] Appl. No.: 34,757

[22] Filed: Apr. 6, 1987

[51] Int. Cl.$^5$ .......................... G01N 33/53; C12N 9/96
[52] U.S. Cl. ............................................ 435/7; 435/18; 435/188; 435/810
[58] Field of Search .................... 435/4, 7, 14, 18, 184, 435/188, 195, 810; 436/18, 176, 7, 18, 188

[56] References Cited

U.S. PATENT DOCUMENTS

| | | | |
|---|---|---|---|
| 3,950,223 | 4/1976 | Yugari et al. | 195/68 |
| 4,121,975 | 10/1978 | Ullman et al. | 195/99 |
| 4,378,428 | 3/1983 | Farina et al. | 435/7 |
| 4,708,929 | 11/1987 | Henderson | 435/7 |

FOREIGN PATENT DOCUMENTS

| | | |
|---|---|---|
| 0166601 | 6/1985 | European Pat. Off. . |
| 0085290 | 5/1984 | Japan . |
| 0160884 | 8/1985 | Japan . |
| WO86/02666 | 10/1985 | PCT Int'l Appl. . |
| 2081295A | 1/1981 | United Kingdom . |

OTHER PUBLICATIONS

Szejtli, J., *Industrial Applications of Cyclodextrins* in "Inclusion Compounds III", Academic Press, London, (1984), pp. 287–309.

Turro et al., article in Journal of the American Chemical Society (1982) 104:1789–1794.

J. W. Callahan, et al., Chemical Abstracts, vol. 85, No. 1, (1976), Effects of Detergents on the Hydrolysis of Glycolipids by $\beta$-Galactosidase, p. 145.

A. Hersey, et al., Chemical Abstracts, vol. 106, No. 3, (1987), Mechanism of Inclusion Compound Formation for Binding of Organic Dyes, Ions, and Surfactants $\alpha$-Cylodextrin Studied by Kinetic Methods Based on Competition Experim., p. 18965.

*Primary Examiner*—Esther M. Kepplinger
*Assistant Examiner*—Toni R. Scheiner
*Attorney, Agent, or Firm*—Richard L. Neeley

[57] ABSTRACT

A method of stabilizing $\beta$-galactosidase peptide fragments against storage degradation for use in a complementation assay which comprises storing the peptide fragment in a storage medium containing an ionic surfactant or a surfactant derived from a sugar residue and adding a cyclodextrin to the storage medium after storing the peptide fragments but before using them in a complementation assay.

10 Claims, 3 Drawing Sheets

REAGENT STABILIZATION IN ENZYME-DONOR AND ACCEPTOR ASSAY

BACKGROUND OF THE INVENTION

Field of the Invention

This invention relates to techniques and compositions useful for stabilizing reagents utilized in specific binding assays, such as immunoassays, that utilize enzyme complementation to generate a detectable signal.

Description of the Background

A number of immunoassays and other binding assays have recently been described that utilize the reassociation of polypeptide fragments to form active enzymes as a step of generating a detectable signal utilized to determine the amount of analyte present in an assay mixture. Several of these assays propose utilizing the enzyme β-galactosidase as the enzyme being formed by complementation.

However, the stability of reagents based on fragments of β-galactosidase has been discovered to be less than desirable. There is a gradual and significant loss of activity of the reformed enzyme as storage time of the fragments increases.

Accordingly, there remains a need for stabilization of reagents utilized in enzyme complementation assays based on the enzyme β-galactosidase.

RELEVANT PUBLICATIONS

An immunoassay system based on the reassociation of polypeptide fragments is described by Farina and Golkey, U.S. Pat. No. 4,378,428, issued Mar. 20, 1983, and by Gonelli et al., *Biochem. and Biophys. Res. Commun.* (1981) 102:917-923. The molecular nature of β-galactosidase α-complementation is described in a Ph.D. thesis of this title by Langley, UCLA, 1975. An assay system based on natural and modified β-galactosidase polypeptides in a complementation assay is described in PCT Application No. PCT/US85/02095, having an international publication date of May 9, 1986.

SUMMARY OF THE INVENTION

The present invention provides techniques for stabilizing peptide fragments from β-galactosidase prepared for utilization in an α-complementation assay. The peptide fragment is stabilized in a solution containing an ionic surfactant or a surfactant derived from a sugar residue. Since the presence of surfactant is generally not compatible with the complementation of the enzyme acceptor and enzyme donor, excess surfactant must be neutralized or removed. In a preferred embodiment of the invention, selected surfactants are neutralized with a cyclodextrin.

DESCRIPTION OF SPECIFIC EMBODIMENTS

Figure 1:
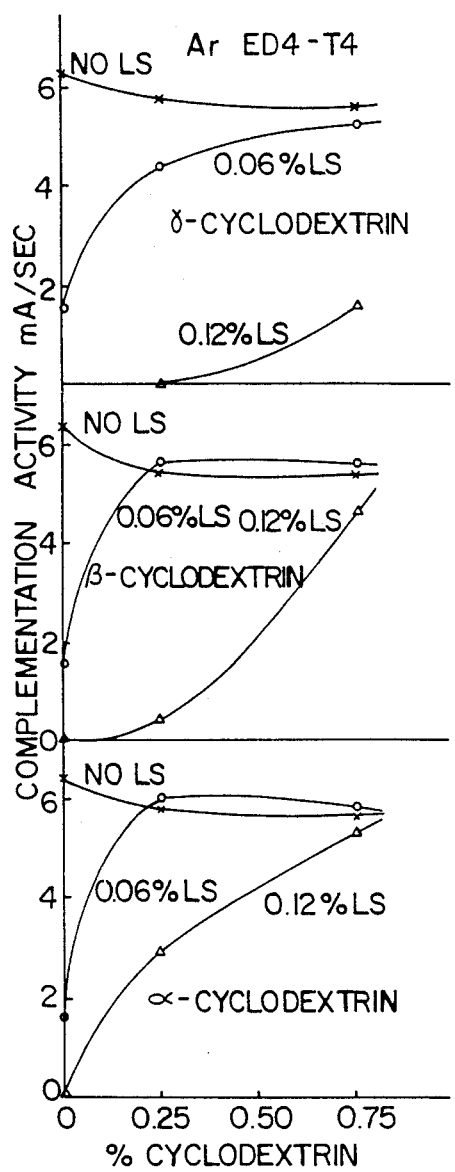
Figure 1:
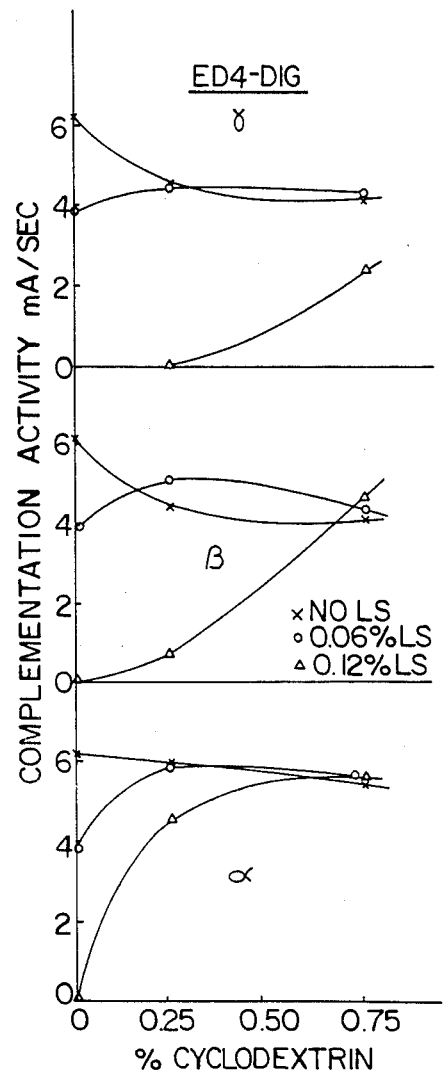

The present invention provides compositions in which β-galactosidase peptide fragments from the α-region of the enzyme are stabilized against loss of activity during storage degradation. It has been discovered that utilizing an ionic surfactant in the fragment-storage medium reduces degradation that normally occurs during storage. If a cyclodextrin is added to the storage or assay medium after storage but prior to carrying out the complementation assay, deleterious effects of the surfactant on the reforming of the active enzyme are avoided. Similar improved results can be achieved by carrying out the complementation assay in the presence of a relatively high concentration of serum, where the serum proteins provide the desired neutralization of the detergent.

The present invention arose out of studies involving complementation assays utilizing β-galactosidase. It was discovered that storage of peptide fragments utilized in the complementation assay resulted in a loss in the activity of the reformed enzyme at a rate of 6-10% per day. By adding, for example, an ionic surfactant to the storage medium, daily losses of activity were reduced to less than 1%, often less than 0.5%. Although use of a surfactant interfered to some extent with the reformation of the active enzyme, the adverse affects of the surfactant could be counteracted by including a relatively high concentration of serum, preferably at least 10%, in the complementation reaction solution or by including a cyclodextrin to clathrate and thereby remove the surfactant.

Several classes of ionic surfactants and surfactants derived from sugar residues have been identified as providing superior storage stability. These include fatty sulfonates, fatty acid amides of amino acids, fatty acid esters of sugars and sugar acid amides, and sulfonate-containing derivatives of cholic acid amides. The fatty (i.e., hydrocarbon) portion of these molecules preferably is derived from a saturated fatty acid having at least 10 but not more than 22 carbon atoms, more preferably in the range of 12-18 carbon atoms. The amino acid portion is preferably a non-polar, genetically encoded amino acid to which the fatty acid portion is attached by means of an amide bond between the carboxylic acid functional group of the fatty acid and the amino functional group of the amino acid. The resulting amide nitrogen can optionally be alkylated, preferably with a methyl group. A particularly useful fatty acid amide of an amino acid is N-lauroylsarcosine (N-dodecanoyl-N-methylglycine).

When a fatty acid forms an ester with a sugar or sugar acid amide, the same fatty acids are preferred as for fatty acid amides of amino acids. The sugar portion is preferably derived from an aldose or an aldonic acid amide, in both cases preferably being derived from glucose, manose, galactose, or the corresponding aldonic acids. Specific examples include decanoyl N-methylgluconamide.

Sulfonate-containing derivatives of cholic acid amides preferably have a sulfonate group attached through a linking organic group to either the amide nitrogen of a cholic acid amide or the 3 α-hydroxy position of a cholic acid compound. Preferred are C2-C5 N-sulfonoalky derivatives of cholamide and N-sulfonoalky derivatives of aminoalkyl ethers attached to the 3-α-hydroxy of cholamide. In both cases the amide or amino nitrogens can be alkylated by lower alkyl groups. In the case of sulfonoalkylated amines, the amino group can be quaternary in order to provide a zwitterionic surfactant. Specific examples include 3-[(3-cholamidopropyl)dimethylammonio]-1-propane sulfonate, 3-[(3-cholamidopropyl)dimethylammonio]-2-hydroxy-1-propanesulfonate, and taurodeoxycholic acid. The first two of these cholic acid derivatives are available commercially under the designations CHAPS and CHAPSO. Taurodeoxycholic acid is often known by the abbreviation TDA.

It has been found that surfactants will increase the stability of β-galactosidase peptide fragments and their conjugates, particularly the donor fragment from the α-region used in complementation assays, in proportion to their relative concentration. Even extremely small amounts of surfactants will result in small increases in storage stability. Since the stabilizing effect varies somewhat with different surfactants, the amount necessary for increasing stability to an acceptable level can most readily be determined by a simple experiment in which different amounts of surfactant are added to a peptide fragment solution. Aliquots are removed at time intervals, the enzyme is reconstituted, and the activity of the resulting reconstituted enzyme is compared to the initial value of a control sample which is utilized to set the 100% enzyme activity level.

Since surfactants slow the degradative processes but do not necessarily halt all degradative processes, some enzyme activity continues to be lost even when a surfactant is used to stabilize the peptide fragment solutions. However, it is generally possible to achieve stabilization sufficient to provide a reconstituted enzyme at 90% of the original activity after six weeks storage utilizing any of the preferred types of surfactants discussed above. Without surfactants, $\beta$-galactosidase peptide fragments from the $\alpha$-region stored for six weeks and reconstituted to form an active enzyme provide only about 25–35% of the activity of reconstituted enzyme prepared without storage.

When utilizing a fatty acid amide of an amino acid, surfactant concentrations of from 0.03 to 0.4%, preferably from 0.06 to 0.18%, can be utilized as initial concentrations and adjusted upward or downward should such adjustment be desirable under the totality of the circumstances. This and all other percentage concentrations expressed herein are weight/volume (w/v) unless otherwise stated. When utilizing a fatty acid ester of a sugar or sugar acid amide, the corresponding concentrations are from 0.15 to 1.5%, preferably from 1.0 to 1.5%. For a sulfonate-containing derivative of a cholic acid amide, the corresponding concentrations are from 0.06 to 0.48%, preferably from 0.12 to 0.24%, for non-zwitterionic forms and from 0.2 to 1.8%, preferably from 0.9 to 1.8%, for zwitter-ionic forms. For fatty sulfonates, from 0.006 to 0.12%, preferably from 0.03 to 0.12%.

The method of the invention can be carried out to stabilize fragments from the amino terminus of $\beta$-galactosidase enzymes. $\beta$-Galactosidase is a tetrameric protein having a molecular weight equal to 540,000 Daltons. The four identical monomers consist of 1021 amino acids, each with a molecular weight of 116,000 Daltons. The monomeric protein is divided into three regions: (1) the N-terminal proximal segment (the $\alpha$-region) (2) a middle region; and (3) a C-terminal distal segment (the $\omega$-region). Complementation assays are generally carried out by utilizing two peptide fragments from $\beta$-galactosidase, a fragment from the $\alpha$-region, typically referred to as the enzyme donor, and a larger fragment that is missing peptides from the $\alpha$-region, typically known as an enzyme acceptor. The ability of peptide fragments to reform into an active enzyme is known as complementation, specifically $\alpha$-complementation when a deletion in the $\alpha$-region in one peptide is complemented by a smaller peptide containing amino acids from the $\alpha$-region. An example of $\alpha$-complementation is provided by the M15/CNBr2 complementation system. The M15 mutant polypeptide lacks amino acids 11–41 of $\beta$-galactosidase and exists in solution as an enzymatically inactive dimer. A polypeptide derived from $\beta$-galactosidase by cyanogenbromide (CNBr) cleavage, the CNBr2 peptide, consists of amino acids 3–92 from $\beta$-galactosidase. The CNBr2 peptide, when mixed with dimer M15, promotes spontaneous reconstitution of the $\beta$-galactosidase tetramer with full enzymatic activity (Langley and Zabin, *Biochemistry* (1976) 15:4866). The M15 peptide is known as an $\alpha$-acceptor and the CNBr2 peptide as an $\alpha$-donor. The CNBr2 peptide can also serve as an $\alpha$-donor for the M112 dimer, a deletion mutation missing amino acids 23–31 within $\beta$-galactosidase (Lin et al., *Biochem. Biophys. Res. Comm.* (1970) 40:249; Celeda and Zabin, *Biochemistry* (1979) 18:404; Welphy et al., *J. Biol. Chem.* (1981) 256:6804; Langley et al., *PNAS USA* (1975) 72:1254). A large number of 60-region fragments of $\beta$-galactosidase useful in complementation assays is described in PCT Application No. PCT/US85/02095, which has an international publication date of May 9, 1986. These mutant fragments comprise two domains, an $\alpha$-donor domain containing a protein sequence capable of combining with an enzyme-acceptor to form an active $\beta$-galactosidase enzyme, and an analyte domain capable of interacting with an analyte-binding protein to provide means for conjugating an analyte to the enzyme donor. These enzyme-donor fragments, in combination with enzyme-acceptor fragments (which, as described above, consist of proteins prepared from mutant genes having deletion mutations within the $\alpha$-region, or being otherwise prepared to provide deletions in the amino acids of the $\alpha$-region) are capable of reconstituting to form active $\beta$-galactosidase enzyme.

Further stabilization of reagents utilized in $\beta$-galactosidase complementation assays can be achieved by adding a chelating agent to the storage medium containing the enzyme-acceptor reagents. These fragments, consisting of a polypeptide containing the complete middle region and C-terminal region of a $\beta$-galactosidase enzyme, typically have a number of cystine residues and are stabilized when protected against metal-catalyzed oxidation. Addition of a chelating agent for metal ions, such as EDTA or EGTA, increase stability of peptide fragments from these portions of the $\beta$-galactosidase enzyme.

The storage medium in which peptide fragments are stored can contain, in addition to the surfactants as described above, other components useful for a variety of purposes. For example, a buffer may be present in the storage media so that simple mixing of the storage media and a sample will provide a medium having the pH desired for optimum activity of the reconstituted $\beta$-galactosidase enzyme. A bacteriocide, such as sodium azide, can be present to prevent growth of bacteria. Other components that may be present include but are not limited to magnesium ions or other ions necessary for enzyme activity, reagents intended to prevent degradation of cystine residues such as dithiothrietol (DTT), solublizing agents such as solvents (e.g., ethylene glycol), and non-ionic surfactants (e.g., fatty acid esters of condensation products of sorbitol and ethyleneoxide, such as Tween 20). The storage medium is typically aqueous with the $\beta$-galactosidase peptide fragment being present at concentrations from about 5–100 nM, preferably from about 10–50 nM.

Although surfactants contribute to stability of the enzyme fragment during storage, they interfere with the complementation assay since surfactants act to denature proteins and the proteins must refold to their correct conformation in order to form an active enzyme. Since the reaction medium for a complementation assay contains components other than the enzyme donor storage medium, the resulting dilution aids somewhat in reducing the effect of the surfactants added to the enzyme donor storage medium. For example, a thirty-fold dilution of a storage medium containing about 0.06% sodium dodecylsulfate allowed complementation. However, dilution and the resulting decrease in concentration of reagents is less desirable than a technique that would allow the reaction to occur undiluted. To this end, techniques for removing surfactants from the complementation assay medium were investigated. It has been found that addition of a cyclodextrin to the assay medium counteracts the effect of the surfactant and allows the complementation assay to proceed without dilution.

Cyclodextrins are cyclic amyloses. α-Cyclodextrin is cyclohexaamylose, β-cyclodextrin is cycloheptaamylose, and γ-cyclodextrin is cyclooctaamylose. These cyclic amyloses form inclusion compounds (clathrates) and are capable of trapping a number of different organic molecules. However, their use to trap surfactants and thereby remove surfactants from peptide surfaces was not known prior to this aspect of the present invention being discovered.

Although all three of the cyclodextrins are effective in removing any of the surfactants utilized to stabilize fragments of β-galactosidases, advantages are achieved by matching the size of the surfactant to the size of the interior space of the cyclodextrin. Surfactants derived from cholic acid derivatives are therefore most readily removed using γ-cyclodextrin, which has the largest interior space. Smaller surfactants, such as fatty acid amides of amino acids and fatty sulfonates are most readily removed with α-cyclodextrin, which has the smallest interior space of the three cyclodextrins.

The use of any amount of cyclodextrin reduces the extent to which dilution of the assay medium is required, and therefore any use of cyclodextrin to remove surfactant from a complementation assay medium falls within the scope of the broadest aspects of the present invention. However, it is preferred to provide a molar ratio of cyclodextrin to surfactant of at least 1:1, preferably at least 2:1. Since cyclodextrins themselves have some adverse affect on the complementation assay, it is preferred to utilize no more than a slight excess of cyclodextrin over the amount required to neutralize the effect of surfactant. This amount can readily be determined by simple experimentation utilizing various dilutions of cyclodextrin for any given concentration of surfactant. It is preferred to keep the upper limit of the molar ratio of cyclodextrin to surfactant below 8:1, preferably below 4:1. These limits can be adjusted as desired depending on the totality of circumstances.

It has been found that serum also acts to neutralize the effect of surfactants. Even in the absence of cyclodextrins, reactions run in relatively high concentrations of serum allow complementation to occur more readily than reactions carried out in low serum concentrations. Serum concentrations of at least 5%, preferably at least 10% of the total assay volume used in the complementation step of the assay are sufficient to allow complementation to proceed to a measurable extent.

The invention now being generally described, the same will be better understood by reference to the following examples which are provided for purposes of illustration and are not to be considered limiting of the invention unless so specified.

EXAMPLES

The following abbreviations and trade names are utilized in the following examples to indicate specific surfactants: LS=N-lauroylsarcosine (also known as N-dodecanoyl-N-methylglycine); CHAPS=3-[(3-cholamidopropyl)dimethylammonio]-1-propanesulfonate; CHAPSO=3-[(3-cholamidopropyl)dimethylammonio]-2-hydroxy-1-propanesulfonate; TDA=-taurodeoxycholic acid (also known as $3\alpha,12\alpha$-dihydroxy-$5\beta$-cholan-24-oic acid N-[2-sulfoethyl]amide; Mega 10=N-decanoyl-N-methylglucamide; Brij 99=a trade name of an oleyl ether of polyoxyethylene containing an average of 20 oxyethylene units; Triton X67=a trade name for a solid flake polyoxyethylene fatty acid ether (non-ionic) of unspecified structure; Brij 96=a trade name of an oleyl ether of polyoxyethylene containing an average of 10 oxyethylene units; Lubrol PX=a trade name for ethyleneoxide condensates of fatty alcohols (the exact structure unspecified); Nonidet P-40=a trade name for an octalphenol-ethyleneoxide condensate containing an average of 9 moles ethylenoxide per mole of phenol; and Tween 20=a trade name designating the condensation product of an ether of polyoxyethylene and sorbitol with dodecanoic acid and other fatty acids.

EXAMPLE 1

Variation in Stability of Enzyme Donors with Variation in Amount of Sodium Dodecylsulfate Present Four sets of assays were run utilizing an enzyme donor molecule with three different antigens or without any antigen. The basic enzyme donor, identified as ED4, consists of N-terminal residues 6-51 with certain restriction site peptides attached to the amino and carboxyl terminals. The three antigens attached to the basic enzyme donor were T4, digoxin, and theophylline. Attachment was by maleimide linkage between the antigen and a cystine residue at position 46 of the polypeptide. Initial enzyme donor concentrations were 25 nM ED4, 20 nM ED4-T4, 20 nM ED4-Dig, 40 nM ED4-Theo.

A storage buffer consisting of 150 mM $KPO_4$, 100 mM $NaPO_4$ ("$KPO_4$" and "$NaPO_4$" are designations for mixtures of $K_2HPO_4$ and $KH_2PO_4$ (or the corresponding sodium salts) balanced to provide a pH of 7.0), 10 nM EGTA (ethyleneglycol-bis-($\beta$-aminoethyl ether)-N,N,N',N'-tetracetic acid), 2 mM $Mg(OAc)_2$, 0.05% Tween 20, 0.05mM DTT (dithiothreitol), 20 mM $NaN_3$, 2.4% ethylene glycol, pH 7.0. The storage container was a clear glass test tube sealed with Parafilm.

Enzyme donor stability was determined by conducting a complementation assay utilizing 100 $\mu$L 800 nM enzyme acceptor, 10 $\mu$L 20 nM enzyme donor, 190 $\mu$L 0.6 mg/ml CPRG (chlorophenol red $\beta$-D-galactopyranoside, a $\beta$-galactosidase substrate); the enzyme donor and sodium dodecyl sulfate was diluted 30-fold in this assay. Enzyme activities were measured prior to storage (day 0) and after storage of the components at 30° C. for 1, 5, 8, 15, 21, and 41 days.

All four ED4-X reagents (three conjugates and the control, an unmodified enzyme donor) showed a loss enzyme activity upon complementation with time. At 41 days all enzyme activity levels were in the range of from 30–40% of original activity in the absense of stabilizers.

Additional experiments were then run to determine whether added sodium dodecylsulfate (SDS) would maintain activity of the reconstituted enzyme formed by complementation. Although anomalous results attributable to experimental error were noted with lower concentrations of added SDS in some instances, there was a general trend of increased storage stability with increasing amounts of SDS. Concentrations of 0.06%, 0.015%, 0.03%, and 0.015% were required to maintain enzyme activity at the level of 90% or greater of original activity at 41 days for ED4-T4, ED4-Dig, ED4-Theo, and ED4, respectively.

There is an apparent activation of ED4 in the presence of SDS. The denaturation caused by the surfactant may allow a more stable, less active form of ED4 (present in the absence of surfactant) to refold in a more active configuration upon dilution during the complementation assay. The ED4 conjugates do not show this apparently anomalous behavior, possible because they are more restricted in the configurations that they may exist in as the result of attachment of the antigen to form the conjugate. This theory is not proven but may be helpful in understanding the results set forth in these experiments.

EXAMPLE 2

Effects of Different Surfactants on ED4-T4 Stability

A number of different surfactants were tested for their effect on storage stability of ED4-T4 utilizing the same storage buffer, storage container and storage temperature set forth in Example 1. ED4-T4 concentration was 20 nM and storage time was limited to eight days. Enzyme activity was assayed in the same manner as in Example 1.

Results are set forth in Table 1 below.

TABLE 1

| Additive | Conc. in Reagent | Conc. During Assay | % Activity After 8 Days |
|---|---|---|---|
| N-Lauroylsarcosine | 0.24% | 0.008% | 95 |
| CHAPS | 0.9% | 0.03% | 83 |
| Taurodeoxycholic Acid | 0.24% | 0.008% | 86 |
| Mega 10 | 1.5% | 0.05% | 80 |
| NaSCN | 1 M | 33 mM | 75 |
| CHAPSO | 0.9% | 0.03% | 78 |
| Octyl $\beta$-Glucoside | 0.9% | 0.03% | 75 |
| Deoxycholic Acid | 0.12% | 0.004% | 53 |
| Brij 99 | 0.09% | 0.03% | 67 |
| Triton X67 | 0.09% | 0.03% | 62 |
| Control | — | — | 65 |
| Brij 96 | 0.45% | 0.015% | 62 |
| Tween 20 | 0.9% | 0.03% | 62 |
| Lubrol Px | 0.24% | 0.008% | 62 |
| Nonidet P-40 | 0.24% | 0.008% | 33 |

The best stability was achieved with N-Lauroylsarcosine, CHAPS, Taurodeoxycholic Acid, and Mega 10 at the indicated concentrations. A number of nonionic surfactants, as indicated in the table, either showed no appreciable effect or detrimental effects.

EXAMPLE 3

Effect of Surfactants on ED4 Stability

The effect of different surfactants on ED4 stability was determined using the same reaction conditions set forth in Example 2. An ED4 concentration of 25nM was utilized. The results are shown in Table 2.

TABLE 2

| Additive | Conc. in Reagent | Conc. During Assay | % Activity After 8 Days |
|---|---|---|---|
| N-Lauroylsarcosine | 0.24% | 0.008% | 114 |
| CHAPS | 0.9% | 0.03% | 93 |
| Taurodeoxycholic Acid | 0.24% | 0.008% | 93 |
| Mega 10 | 1.5% | 0.05% | 87 |
| NaSCN | 1 M | 33 mM | 90 |
| CHAPSO | 0.9% | 0.03% | 88 |
| Octyl $\beta$-Glucoside | 0.9% | 0.03% | 85 |
| Deoxycholic Acid | 0.12% | 0.004% | 73 |
| Brij 99 | 0.09% | 0.03% | 72 |
| Triton X67 | 0.09% | 0.03% | 73 |
| Control | — | — | 75 |
| Brij 96 | 0.45% | 0.015% | 72 |
| Tween 20 | 0.9% | 0.03% | 70 |
| Lubrol Px | 0.24% | 0.008% | 60 |
| Nonidet P-40 | 0.24% | 0.008% | 17 |

The best stability was achieved with N-lauroylsarcosine, CHAPS, taurodeoxycholic acid, and sodium thiocyanate at the indicated concentrations. Some activation (similar to that seen with SDS in Example 1) was seen for N-lauroylsarcosine.

EXAMPLE 4

Effects of Various Surfactants and Chaotropic Conditions on ED4-T4 Stability

The effect of various surfactants and chaotropic conditions on ED4-T4 stability was determined under the same conditions set forth in Example 2. The ED4-T4 concentration was 20 nM. Enzyme activity was measured at days 0, 1, 5, 8, 14, and 34.

N-lauroylsarcosine, taurodeoxycholate, CHAPS, and NaSCN were tested at different concentrations. Enzyme activities of at least 90% of the original activity was obtained with minimum concentrations of 0.06% N-lauroylsarcosine, 0.24% taurodeoxycholic acid, and 1 molar sodium thiocyanate. At 34 days, CHAPS did not support stability of $\geq 90\%$. The absence of stabilizer caused enzyme activity to drop into the range of from 22–34% of original activity in all cases. There was a general trend in all cases of increasing stability with increasing amounts of the indicated surfactant or chaotropic condition (sodium thiocyanate).

EXAMPLE 5

Effect of Various Surfactants or Chaotropic Conditions on ED4 Stability

The effect of various surfactants or sodium thiocyanate on ED4 stability was measured in an experiment similar to that reported in Example 4. The ED concentration was 25 nM. The measuring times and surfactants are the same as those reported in Example 4.

The same general trends were seen. Retention of at least 90% original enzyme activity or greater was obtained with minimum concentrations of 0.03% N-lauroylsarcosine, 0.24% taurodeoxycholic acid, 1.8% CHAPS, and 1M sodium thiocyanate. Stability in the absence of stabilizer was in the range of from 47–57%.

EXAMPLE 6

Effect of Various Substances on ED4-T4 Stability

The effect of a number of different denaturants and solvents on ED4-T4 stability was determined in an assay similar to that described in Example 4. The ED4-T4 concentration was 20 nM, and storage stability was measured for 14 days. The results are set forth in Tables 3 and 4.

TABLE 3

| Additive | Conc. in Storage | Conc. During Assay | % Activity After 14 Days |
| --- | --- | --- | --- |
| SDS | 0.006% | 0.0002% | 69 |
| Propylene Glycol | 4% | 0.13% | 50 |
| Methanol | 5% | 0.17% | 49 |
| Carbitol | 2.5% | 0.083% | 47 |
| Urea | 0.4 M | 13 mM | 51 |
| DMSO | 4% | 0.13% | 44 |
| Ethylene Glycol | 5% | 0.17% | 46 |
| Control | — | — | 44 |
| Guanidine-HCl | 100 mM | 3.3 mM | 45 |
| Acetonitrile | 5% | 0.17% | 42 |
| Sulfolane | 0.75% | 0.025% | 41 |
| DMF | 3% | 0.10% | 5 |

TABLE 4

| Additive | Conc. in Storage | Conc. During Assay | % Activity After 14 Days |
| --- | --- | --- | --- |
| SDS | 0.06% | 0.002% | 94 |
| Methanol | 50% | 1.7% | 87 |
| Acetonitrile | 50% | 1.5% | 94 |
| Propylene Glycol | 40% | 1.3% | 79 |
| Ethylene Glycol | 50% | 1.7% | 81 |
| Guanidine-HCl | 1 M | 33 mM | 68 |
| Sulfolane | 7.5% | 0.25% | 66 |
| Urea | 4 M | 133 mM | 66 |
| DMSO | 40% | 1.3% | 68 |
| DMF | 80% | 1.0% | 66 |
| Carbitol | 25% | 0.83% | 54 |
| Control | — | — | 44 |

The best stability was achieved with SDS, methanol, acetonitrile, propylene glycol, and ethylene glycol at the indicated concentrations.

EXAMPLE 7

Neutralization of Surfactant by Cyclodextrins

The ability of α-, β-, and γ-cyclodextrin to neutralize lauroylsarcosine in ED4-T4 and ED4-Dig complementation assays was determined. The storage buffer was the same as that described in Example 1. Assays were carried out immediately (i.e., without storage). The complementation assay was carried out using 100 μL 800 nM enzyme acceptor, 100 μL 2 nM enzyme donor, and 100 μL 1.1 mg/mL CPRG. No dilution was necessary. The results are set forth in FIG. 1.

The left panel of FIG. 1 shows the effect of α-, β-, and γ-cyclodextrin on a complementation assay utilizing ED4-T4 as the enzyme donor. Percent cyclodextrin is graphed versus complementation activity (expressed in mA/sec). When the cyclodextrins were added in the absence of a stabilizing agent, a slight decrease in complementation activity was seen with increasing concentration of each cyclodextrin. Similarly, the presence of lauroylsarcosine as a stabilizing agent in the reagent during storage interferred with the complementation as indicated by the activities at the 0% cyclodextrin axis. Increasing amounts of all types of cyclodextrins were effective in neutralizing the interference of lauroylsarcosine with the complementation assay. α-Cyclodextrin was most effective with γ-cyclodextrin being least effective. Similar results are shown in the right panel, which show the effects of the cyclodextrins on a complementation assay utilizing ED4-Dig in the absence or presence of lauroylsarcosine in the reagent.

EXAMPLE 8

Neutralization of LIDS and Lauroylsarcosine by Serum

Initial investigations demonstrated that serum was potentially useful for neutralization of surfactants in a complementation assay. This potential was verified in an experiment utilizing the same storage buffer as in the previous experiments. However, since storage stability was not being tested, the assay was carried out immediately. Two series of assays were run utilizing either ED4-T4 or ED4-Dig in storage buffer at a concentration of 2.0 nM. The assay mixture contained 100 μL of the enzyme donor in storage buffer, 100 μL of 720 nM enzyme acceptor (EA 1150), 100 μL 0.6 mg/mL CPRG, and 33 μL of serum at various dilutions. Concentrations of serum in the resulting assay solution varied from 0–10% with LIDS and lauroylsarcosine concentrations, varying from 0–0.048 and from 0–0.24%, respectively.

Figure 2:
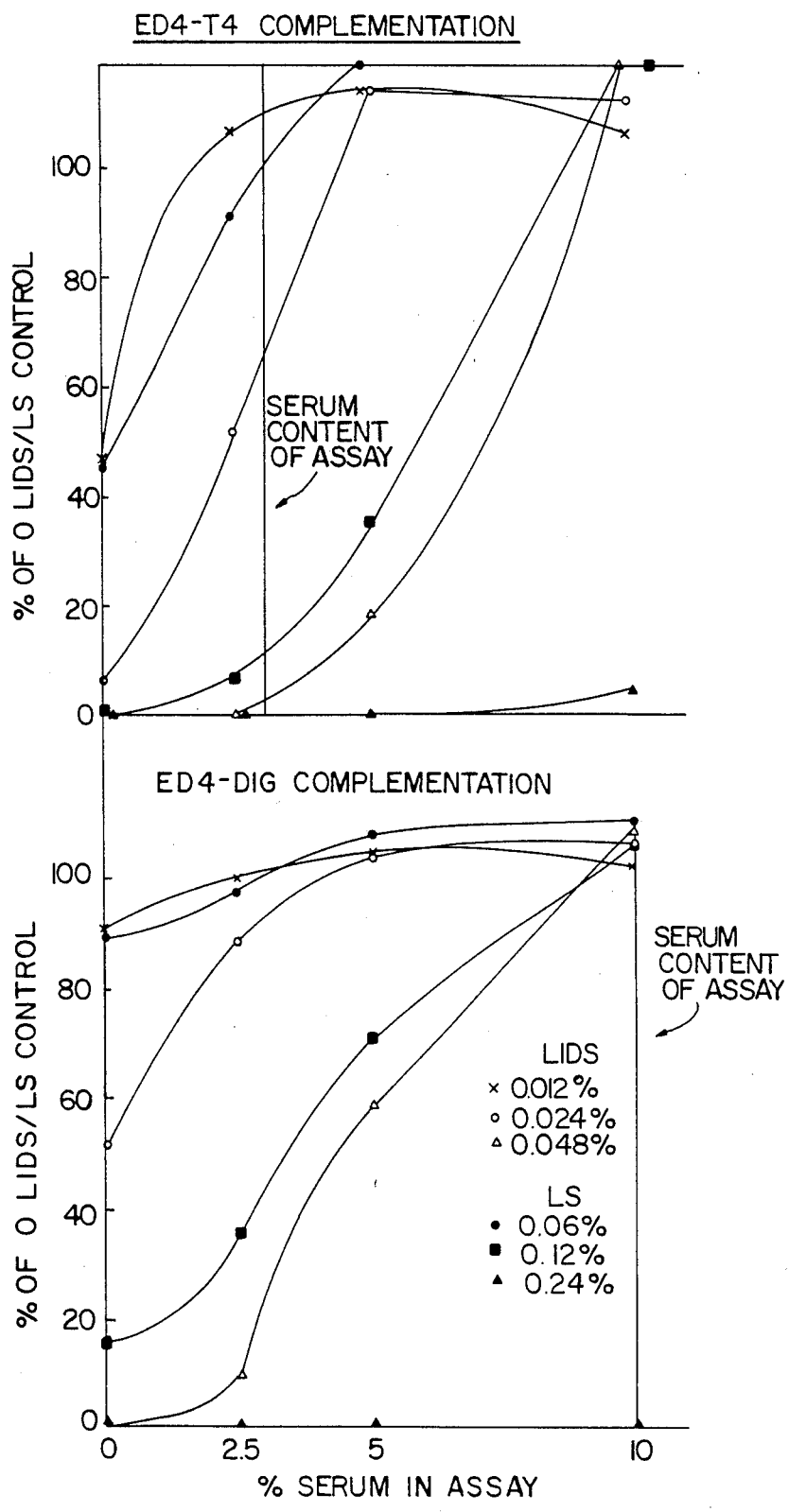

The results are shown in FIG. 2. This figure shows that serum neutralized inhibition of complementation of ED4-T4 and ED4-Dig conjugates caused by both LIDS and lauroylsarcosine. The degree of neutralization depended on the amount of denaturant and serum in the assay. The 10% serum assay for digoxin was completely neutralized under these conditions: the 3.3% serum assay for ED4-T4 demonstrated variable neutralization. Additional neutralization was required for lower-serum-content assays.

EXAMPLE 9

Neutralization of Lauroylsarcosine by α-Cyclodextrin and Complementation Assays

The previous examples of neutralization of surfactants were carried out in relatively simple complementation buffers. When these assays were repeated in a more complex buffer solutions containing, for example (for ED4-T4), 80 mM KPO4, sucrose, ANS (8-anilinonaphthalene sulfonic acid, a thyroxine-releasing agent), methionine, GARS (goat anti-rabbit antiserum), anti-T4 antibody of rabbit origin, and CPRG, pH 7.0, similar results were obtained. α-Cyclodextrin was shown to completely neutralize inhibition of complementation by lauroylsarcosine. The minimum concentration of α-cyclodextrin necessary for complete neutralization of the surfactant varied somewhat with the presence of other assay components. For example, the presence of serum reduced the amount of α-cyclodextrin necessary for complete neutralization. This reaffirms the results set forth above in Example 8. Minimum amounts of α-cyclodextrin required for neutralizing the maximum concentration of lauroylsarcosine tested (0.18%) varied from 0.6% for an ED4-Dig assay containing no serum to 0.1% for an ED4-Dig assay containing 10% serum. Similar results were seen for ED4-T4 assays; an α-cyclodextrin concentration of 0.2% was sufficient to completely neutralize 0.18% lauroylsarcosine in an assay medium containing 3.3% serum, while an α-cyclodextrin concentration of greater than 0.3% was required in the absence of serum.

EXAMPLE 10

Neutralization of Lauroylsarcosine by β-cyclodextrin in Complementation Assays

Figure 3:
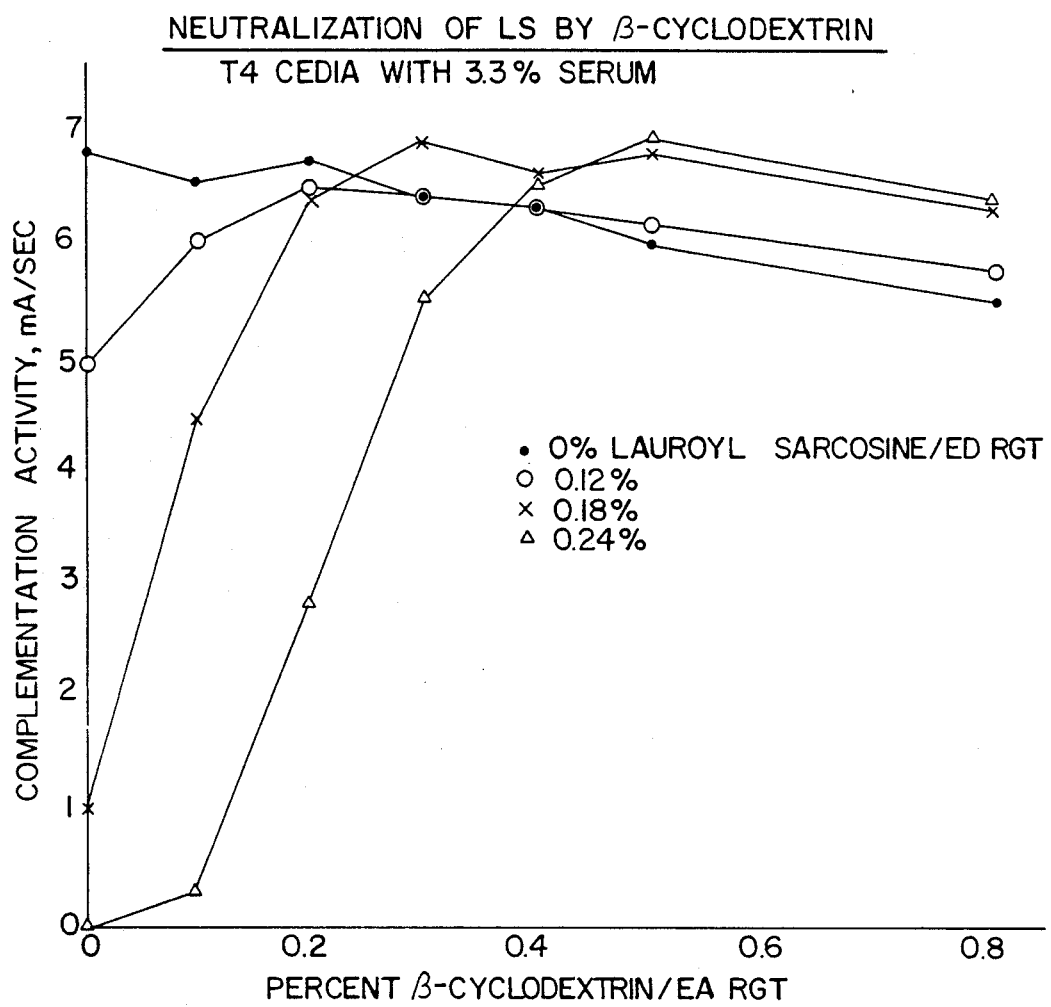

The ability of β-cyclodextrin to neutralize lauroylsarcosine was demonstrated in a complete assay medium containing 80 mM KPO$_4$, 10 mM EGTA, 2 mM magnesium acetate, 20 mM sodium azide, 0.05% Tween 20, 0.05 mM DTT, pH 7.0. The ingredients above were present in both enzyme donor and enzyme acceptor storage solutions. The enzyme donor (ED4-T4) solution also contained 1.4 mg/mL CPRG and 1:52 GARS. The enzyme acceptor solution also contained 5 mM sucrose, 10 mM methionine, 0.3 mM ANS, and a 1:350 dilution of anti-T4 antibody. Assay volumes were 125 μL enzyme acceptor containing variable amounts of β-cyclodextrin, 65 μL enzyme donor containing variable amounts of lauroylsarcosine, 51.6 μL water, and 8.3μL sample. The variable concentrations of lauroylsarcosine and β-cyclodextrin are shown in FIG. 3, which also shows the results of the assay.

β-Cyclodextrin neutralized n-lauroylsarcosine in the presence of 3.3% serum and the remainder of the assay components. These results are similar to those shown in Example 9 for α-cyclodextrins. Although β-cyclodextrin did not interfere with antibody bonding in the ED4-T4 assay, disruption of antibody binding was seen in a digoxin assay.

EXAMPLE 11

Neutralization of Taurodeoxycholic Acid by β-Cyclodextrin in Complementation Assays The ability of β-cyclodextrin to neutralize taurodeoxycholic acid (TDA) was determined using the same assay conditions described in Example 10. β-Cyclodextrin concentrations range from 0–0.8%, taurodeoxycholic acid concentrations ranged from 0–0.48%, and serum concentrations ranged from 0–10%. The results were similar to those for lauroylsarcosine, but β-cyclodextrin was less effective at any given concentration. The higher concentrations of taurodeoxycholic acid could not be effectively neutralized within the solubility range of β-cyclodextrin. However, lower concentrations could be effectively neutralized. TDA at 0.12% was effectively neutralized at 0.4% β-cyclodextrin; TDA at 0.24% was neutralized at 0.8% β-cyclodextrin.

In a similar experiment utilizing α-cyclodextrin in an attempt to neutralize taurodeoxycholic acid, no neutralization effect of α-cyclodextrin could be demonstrated. On the other hand, γ-cyclodextrin was more effective than β-cyclodextrin in neutralizing TDA. Based on the other results shown here, this result appears to be explainable by the size of the opening in the cyclodextrins, the γ-cyclodextrin having the largest central space and therefore having the most room available for the steroid ring of taurodeoxycholic acid.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. In a specific binding assay for an analyte utilizing enzyme complementation, wherein a detectable signal is generated upon the reassociation of beta-galactosidase peptide fragments in a reaction mixture to form active enzymes wherein the improvement comprises:
    (a) storing a beta-galactosidase peptide fragment in a storage medium containing an ionic surfactant or a surfactant derived from a sugar residue in an amount sufficient to stabilize said beta-galactosidase peptide fragment against storage loss of complementation activity; and
    (b) adding a cyclodextrin to said storage medium in an amount sufficient to clathrate said ionic surfactant or said surfactant derived from a sugar residue after said storing but prior to using said fragments in said specific binding assay.

2. The method of claim 1, wherein said surfactant is a fatty sulfonate, a fatty acid amide of an amino acid, a fatty acid ester of a sugar or sugar acid amide, or a sulfonate-containing derivative of a cholic acid amide.

3. The method of claim 2, wherein said surfactant is a salt of dodecyl sulfate, N-lauroylsarcosine, 3-[(3-cholamidopropyl)dimethylammonio]-1-propanesulfonate, 3-[(3-cholamidopropyl)dimethylammonio]-2-hydroxy-1-propanesulfonate, taurodeoxycholic acid, or decanoyl N-methylgluconamide.

4. The method of claim 1, wherein said surfactant is present at a concentration of from 0.006 to 1.8%.

5. The method of claim 1, wherein said peptide fragment is a β-galactosidase α-region fragment.

6. The method of claim 1, wherein said cyclodextrin is α- or β-cyclodextrin and said surfactant is N-lauroylsarcosine.

7. The method of claim 1, wherein said cyclodextrin is γ-cyclodextrin and said surfactant is a sulfonate-containing derivative of a cholic acid amide.

8. The method of claim 1, wherein said peptide fragment comprises β-galactosidase amino acid residues 6–51.

9. The method of claim 1, wherein the number of moles of cyclodextrin added to said storage medium is at least equal to the number of moles of surfactant present in said storage medium.

10. The method of claim 1, which further comprises carrying out a complementation assay in a solution containing said surfactant and at least 3.3% serum.

* * * * *